United States Patent [19]

Hauke et al.

[11] Patent Number: 5,551,778
[45] Date of Patent: Sep. 3, 1996

[54] A CYLINDER FOR MIXING COMPONENTS TO FORM BONE CEMENT

[75] Inventors: Gunter Hauke, Muhltal; Rainer Specht, Furth; Ralf Krotz, Wiesloch; Reiner Funk, Munster/Altheim; Peter Martin, Wiesbaden; Berthold Nies, Frankisch-Crumbach, all of Germany

[73] Assignee: Merck Patent Gesellschaft Mit Berschrankter Haftung, Darmstadt, Germany

[21] Appl. No.: 502,556

[22] Filed: Jul. 14, 1995

[30] Foreign Application Priority Data

Jul. 16, 1994 [DE] Germany ............................ 44 25 218.8

[51] Int. Cl.⁶ .................................................. B01F 13/06
[52] U.S. Cl. ......................... 366/139; 366/256; 206/222
[58] Field of Search ................................ 366/129, 130, 366/139, 184, 189, 255, 256–260, 332–335; 206/219, 220, 222; 606/86, 92–94; 604/411, 414–416, 903

[56] References Cited

U.S. PATENT DOCUMENTS

| 44,179 | 9/1864 | Gibson | 366/332 |
|---|---|---|---|
| 2,615,692 | 10/1952 | Muller | 366/332 X |
| 3,197,067 | 7/1965 | Rataczak | 366/333 X |
| 4,463,875 | 8/1984 | Tepic | 222/94 X |
| 4,469,153 | 9/1984 | Morrisette | 366/333 X |
| 4,721,390 | 1/1988 | Lidgren | 366/139 |
| 4,735,509 | 4/1988 | Rausch | 366/184 X |
| 4,758,096 | 7/1988 | Gunnarsson | 366/139 |
| 4,808,006 | 2/1989 | Kaufeler | 366/333 X |
| 4,858,759 | 8/1989 | Mauthe et al. | 206/220 X |
| 4,973,168 | 11/1990 | Chan | 366/255 X |
| 5,252,301 | 10/1993 | Nilson et al. | 366/256 X |
| 5,328,262 | 7/1994 | Lidgren et al. | 366/256 X |

FOREIGN PATENT DOCUMENTS

2800587  7/1979  Germany ............................ 206/219

Primary Examiner—Charles E. Cooley
Attorney, Agent, or Firm—Millen, White, Zelano, & Branigan P.C.

[57] ABSTRACT

A device for mixing and discharging bone cement has a mixing cylinder which consists of two cylinder parts and in which an openworked mixing plunger can be moved axially. The lower cylinder part is sealed off by a discharging plunger. A separating plunger is arranged axially displaceably in the mixing cylinder between the mixing plunger and the discharging plunger, which separating plunger seals off the one cylinder part before the two cylinder parts are connected. The separating plunger has through-flow channels through which a liquid monomer can flow from the lower cylinder part to a pulverulent polymer in the upper cylinder part at the start of the mixing procedure.

15 Claims, 7 Drawing Sheets

A CYLINDER FOR MIXING COMPONENTS TO FORM BONE CEMENT

FIELD OF THE INVENTION

The invention relates to a device for mixing and discharging bone cement, with a two-part mixing cylinder in which an openworked mixing plunger can be moved axially and rotatably by means of an actuation rod emerging in a sealed manner at one cylinder end, the mixing cylinder being closed at the other cylinder end by a releasably locked discharging plunger which can be pressed axially into the mixing cylinder in order to discharge the mixed bone cement through an opposite discharge opening.

BACKGROUND OF THE INVENTION

The starting materials for producing bone cement, namely a pulverulent polymer and a liquid monomer, must be mixed directly before the introduction of the bone cement into the bone. This mixing procedure must therefore be carried out in the operating theatre under sterile conditions.

Different devices have been disclosed for this purpose, a common feature of these being that a mixing cylinder, in which the pulverulent polymer and the liquid monomer are mixed, serves immediately thereafter as a discharging cylinder or cartridge from which the ready-mixed bone cement is pressed out and brought to the application site.

A vacuum is normally generated in the mixing cylinder, either during the mixing procedure or directly thereafter, in order to reduce, at least to a substantial extent, the formation of pores in the bone cement.

In a known device of the generic type mentioned in the introduction (DE 43 02 230 A1), incorporated herein by reference, the starting materials, namely powder and liquid, must be introduced into the mixing cylinder prior to the mixing procedure, and only then is the mixing cylinder closed. By activating the mixing plunger by means of the actuation rod, the materials in the mixing cylinder are thoroughly mixed, during which the discharging plunger is held securely at the cylinder end. When the mixing procedure has been completed, the discharging plunger is released and is pressed as a press plunger into the mixing cylinder. The mixed bone cement is discharged at the opposite cylinder end. In the case where liquid and in particular powder are poured in freely, there is the risk of this material getting into the surrounding environment and leading to contamination, which is undesirable especially under operating conditions. Of particular concern in this respect is the possibility that the powder may lead to dust developing while it is being poured in, and that the liquid monomer may emit vapours. For this reason, it is necessary to pour the starting materials into the mixing cylinder as far away as possible from the operation site.

SUMMARY OF THE INVENTION

The object of the invention is to further develop a device of the generic type mentioned in the introduction in such a way that, on the one hand, the pulverulent polymer and, on the other hand, the liquid monomer can be formulated in advance in such a way that these materials can be made ready in sealed containers and can be brought into the operating area without their having to be transferred again prior to the mixing procedure.

According to the invention, this object is achieved by virtue of the fact that a separating plunger is arranged axially displaceably in the mixing cylinder between the mixing plunger and the discharging plunger, and that the cylinder chambers of the mixing cylinder which are separated from each other by the separating plunger are connected to each other, at least in an area adjacent to the discharging plunger, via at least one through-flow channel.

In preparation for the mixing procedure, the pulverulent polymer is poured into the cylinder part which also has the discharge opening and in which the mixing plunger is situated. This cylinder part is then sealed by the separating plunger.

The liquid monomer is introduced, preferably in a sealed, easy-to-destroy package or cartridge, for example a foil bag, into the other cylinder part which is sealed at the bottom by the discharging plunger.

In this prepared form, the starting materials are kept at the ready in the operating room. Prior to the mixing procedure, the two cylinder parts are connected to one another in order to form the mixing cylinder. By pressing the actuation rod in, the mixing plunger and the separating plunger are displaced in the direction of the discharging plunger, while the mixing cylinder is closed. The liquid monomer, if appropriate after destruction of the package containing the liquid, thus flows through one or more through-flow channels into the discharge-side cylinder chamber containing the powder. By activating the mixing plunger, an intensive mixing of powder and liquid then takes place therein. For the subsequent discharging procedure, the discharging plunger is displaced towards the discharge side, together with the separating plunger situated above it.

The handling of the device is considerably simplified by comparison with known embodiments, because the two material components are made ready in a pre-formulated form, and no transfer of liquid or powder is necessary in the operating room. Contamination in the operating area as a result of dust developing, vapour and/or splashes of liquid is avoided in this way. It is thus possible to provide for pre-formulated charges of the components of the mixture to be held in the two cylinder chambers of the mixing cylinder.

One or more bores are preferably provided in the separating plunger, these bores forming the through-flow channels. It is also possible, instead of this, to form the through-flow channels by means of longitudinal grooves in the inner wall of the mixing cylinder.

According to a preferred embodiment of the invention, the actuation rod is connected in a releasable manner to the mixing plunger, and a guide bush, which is arranged detachably on the mixing cylinder, and through which the actuation rod is guided sealingly, can be replaced by a discharge nozzle.

It is thus possible, upon completion of the mixing procedure, to remove the actuation rod which hampers the discharging procedure. The opening in which the guide bush for the actuation rod was received is then available for receiving a discharge nozzle, so that the formation of a separate discharge opening can be dispensed with.

According to a particularly preferred embodiment of the invention, the releasable connection between the actuation rod and the mixing plunger is formed by a predetermined break point. In this way the actuation rod can be released in a particularly simple manner and without the provision of special coupling elements.

According to a further advantageous embodiment of the invention, an axially movable sealing plunger is arranged between the discharging plunger and the separating plunger. This additional sealing plunger is used to seal off the lower cylinder part, holding the liquid monomer, prior to the mixing procedure. In this case, the one cylinder part containing the pulverulent polymer is sealed off by the separating plunger, and the other cylinder part containing the liquid monomer is sealed off by the sealing plunger, before these two cylinder parts are connected to one another prior to the mixing procedure. When, at the start of the mixing procedure, the separating plunger is displaced in the direction of the discharging plunger in the manner already described, it also carries the sealing plunger along with it.

BRIEF DESCRIPTION OF THE DRAWINGS

Illustrative embodiments of the invention are explained in greater detail hereinbelow and are represented in the drawing, in which.

DETAILED DESCRIPTION

Figure 1:
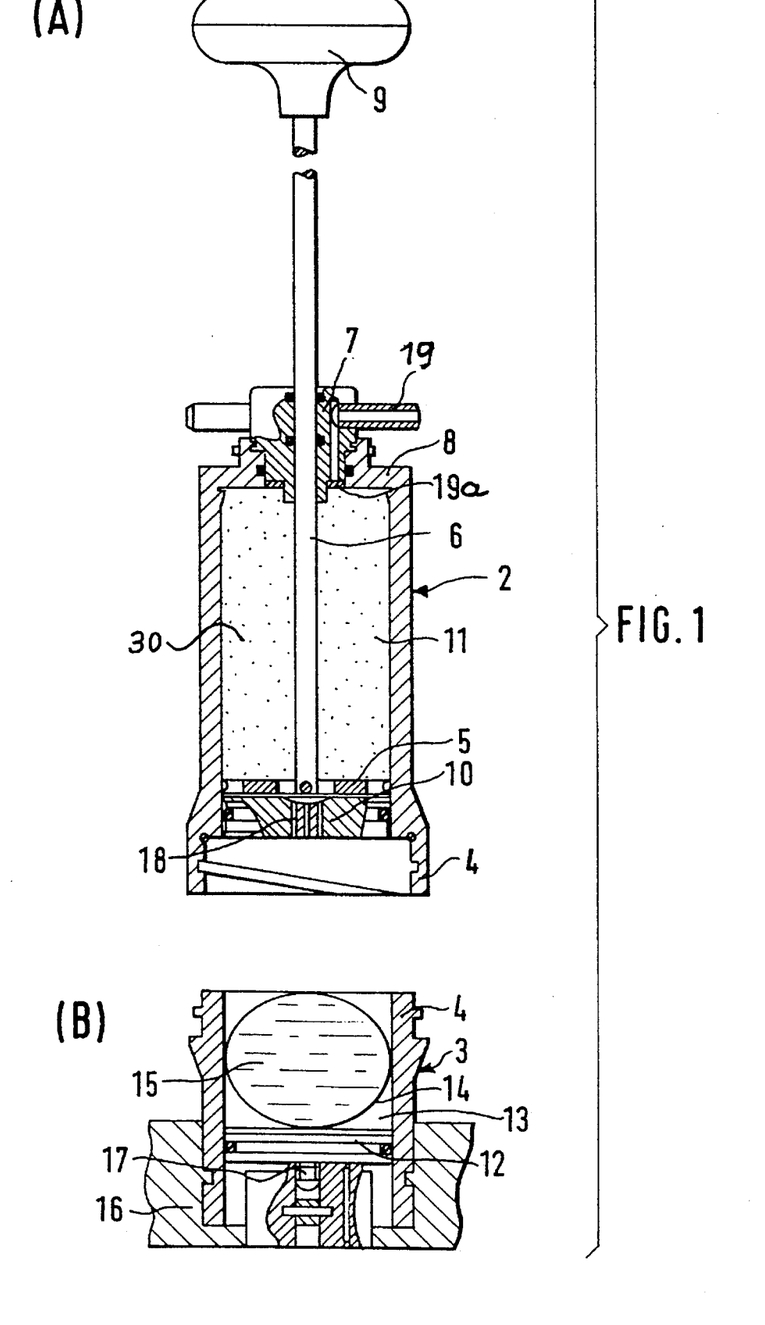
FIG. 1 shows, in a longitudinal section, a device for mixing and discharging bone cement, the two parts of the two-part mixing cylinder being represented separate from one another.

The device shown in FIG. 1 for mixing and discharging bone cement has a two-part mixing cylinder 1 which consists of an upper cylinder part 2 and a lower cylinder part 3. Both cylinder parts 2, 3 can be connected tightly to each other by means of a quick coupling 4, for example by means of a screw connection.

Arranged in the upper cylinder part 2 is a mixing plunger 5 which, in the illustrative example shown, consists of an openworked plate and can be moved axially and rotatably by means of an actuation rod 6. The actuation rod 6 is guided sealingly through a guide bush in the one cylinder end wall 8 and bears an actuation grip 9 at its free end.

Arranged at the lower end of the upper cylinder part 2 is a rigid, imperforable separating plunger 10 which is accommodated in a freely movable manner in the mixing cylinder 1. In the state represented in FIG. 1, ready for a mixing and discharging procedure, the separating plunger 10 forms the lower closure of the upper cylinder part 2. The first cylinder chamber 11 situated above the separating plunger 10 contains a pulverulent polymer 30 as starting material for the bone cement.

The lower cylinder part 3 is sealed at its lower end by a discharging plunger 12 and contains, in the second cylinder chamber 13 situated above the latter, a liquid container 14 in which a second component in the form of a liquid monomer 15 as starting material for the bone cement is enclosed. The liquid container 14 can be, for example, a bag or a cartridge made of an easy-to-destroy material, for example metal foil.

In the initial state, ready for the mixing procedure, as represented in FIG. 1, the lower cylinder part 3 is held in a holding device 16, with the discharging plunger 12 being locked by means of a releasable plunger coupling 17.

The separating plunger 10 has bores 18 which run through the plunger, which form through-flow channels and which, after the two cylinder parts 2 and 3 have been connected, connect to one another the cylinder chambers 11 and 13 which have been separated from one another by the separating plunger 10.

Figure 2:
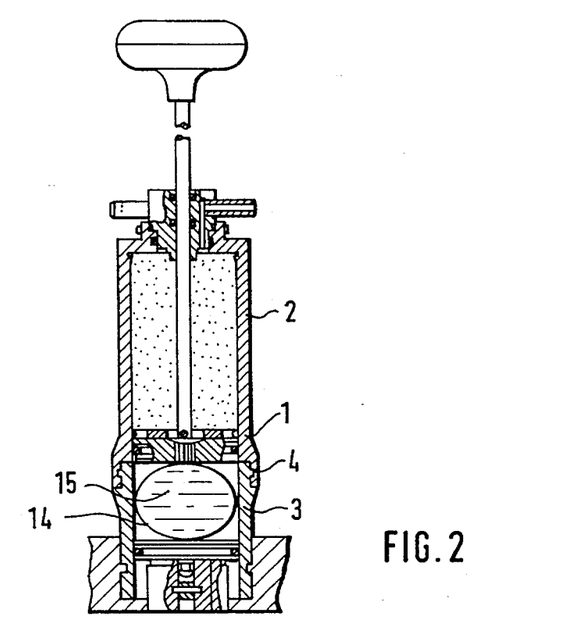
FIGS. 2–5 show successive working positions of the device shown in FIG. 1 during mixing and discharging of bone cement.

As is shown in FIG. 2, the upper cylinder part 2 is connected to the lower cylinder part 3 by means of the quick coupling 4 at the start of the mixing procedure. The mixing plunger 5 is then displaced downwards into the lower cylinder part 3 by means of the actuation rod 6 and the actuation grip 9 (FIG. 3), the mixing plunger 5 carrying the separating plunger 10 along with it. By means of the pressure thereby exerted on the liquid container 14, the latter is destroyed and the liquid monomer 15 contained therein flows through the through-flow channels 18 into the cylinder chamber 11 which is located above it and in which the pulverulent polymer is situated.

The mixing plunger 5 is then moved up and down, and if necessary rotated, using the actuation rod 6 (FIG. 4), as a result of which an, intimate mixing of the pulverulent polymer with the liquid monomer takes place.

Figure 4:
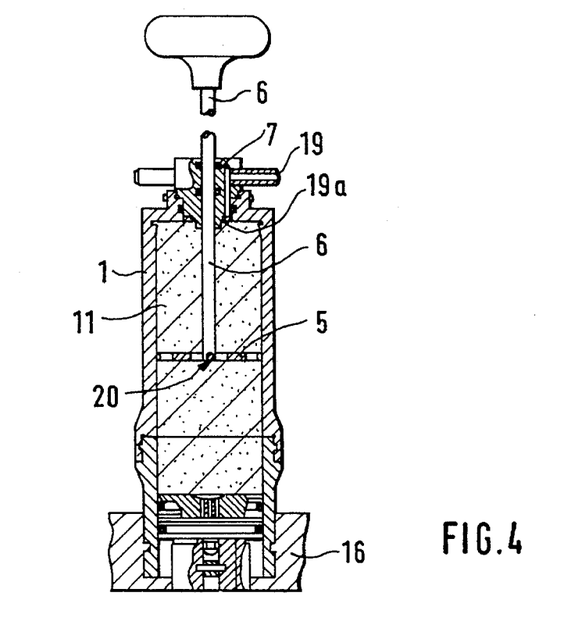

A vacuum line 19 is attached on the guide bush 7 of the actuation rod 6, which vacuum line 19 opens into the cylinder chamber 11 via a filter 19a. By applying a vacuum, a vacuum is created in the cylinder chamber 11 during the mixing procedure, by means of which vacuum the formation of pores in the mixed bone cement is prevented or substantially reduced.

When the mixing procedure has been completed, the actuation rod 6 is separated from the mixing plunger 5. For this purpose, a predetermined break point 20 is provided at the connection point between actuation rod 6 and mixing plunger 5, at which predetermined break point 20 the actuation rod 6 can be released from the mixing plunger 5 by pulling, pressing or turning.

Figure 5:
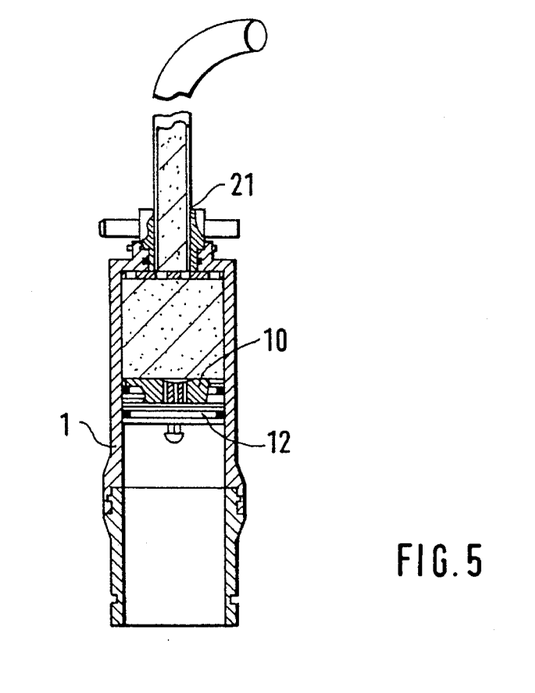

The guide bush 7 is then removed from the mixing cylinder 1 and replaced by a discharge nozzle 21 (FIG. 5). The mixing cylinder 1 is removed from the holding device 16 and is connected to a discharge drive mechanism (not shown), for example a hand press, by means of which the discharging plunger 12 is pressed into the mixing cylinder 1. The discharging plunger 12 carries the separating plunger 10 along with it and presses the mixed bone cement contained in the mixing cylinder 1 out through the discharge nozzle 21.

As an alternative to the illustrative embodiment shown, it is also possible to provide the liquid monomer unsealed in the lower cylinder part 3. Upon connection of the two cylinder parts 2 and 3, the separating plunger 10 closing off the upper cylinder part 2 prevents pulverulent polymer escaping from the upper cylinder part 2 when the two cylinder parts 2 and 3 are connected to one another. Instead of this, the two cylinder parts 2 and 3 can also be provided as pre-formulated cartridges which each contain one of the two starting materials.

The device which has been described can be configured in a vacuum-tight and/or sterilizable design. For example, the whole device can be sterilized after the cylinder parts 2 and 3 have been connected, and before it has been brought to the operating area.

Figure 6:
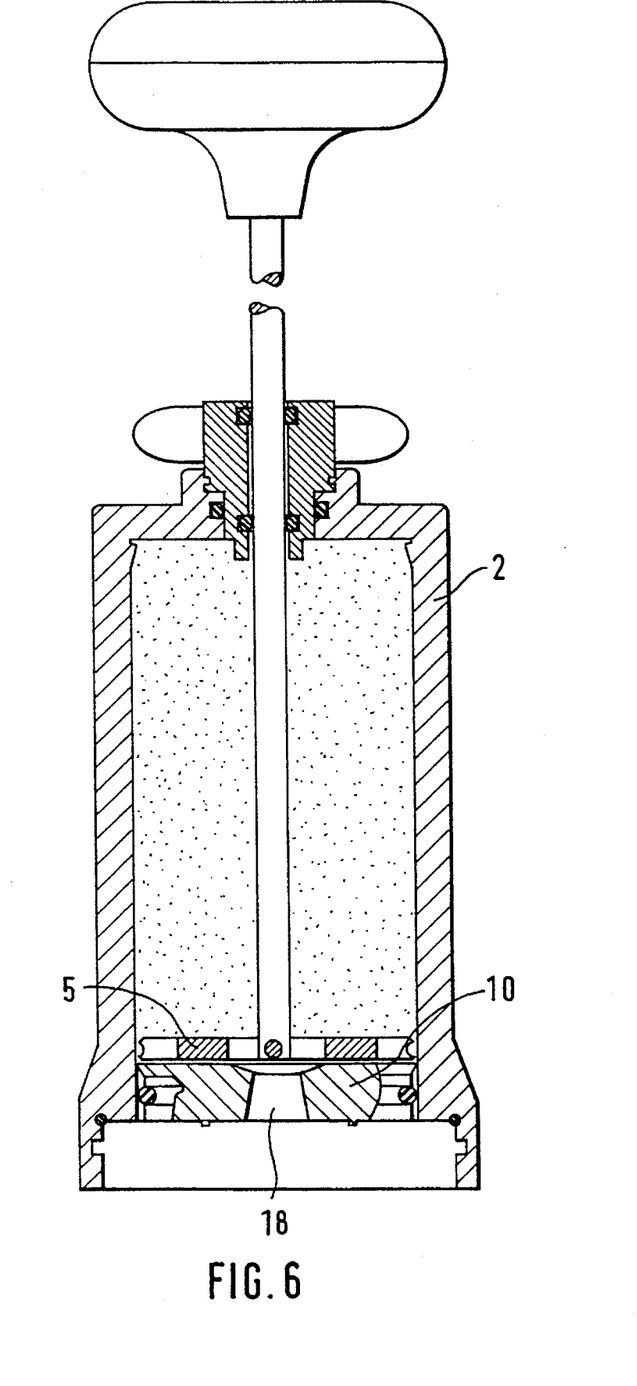
FIGS. 6 and 7 show the two parts of a device, in a design modified in relation to FIG. 1, for mixing and discharging bone cement.
Figure 7:
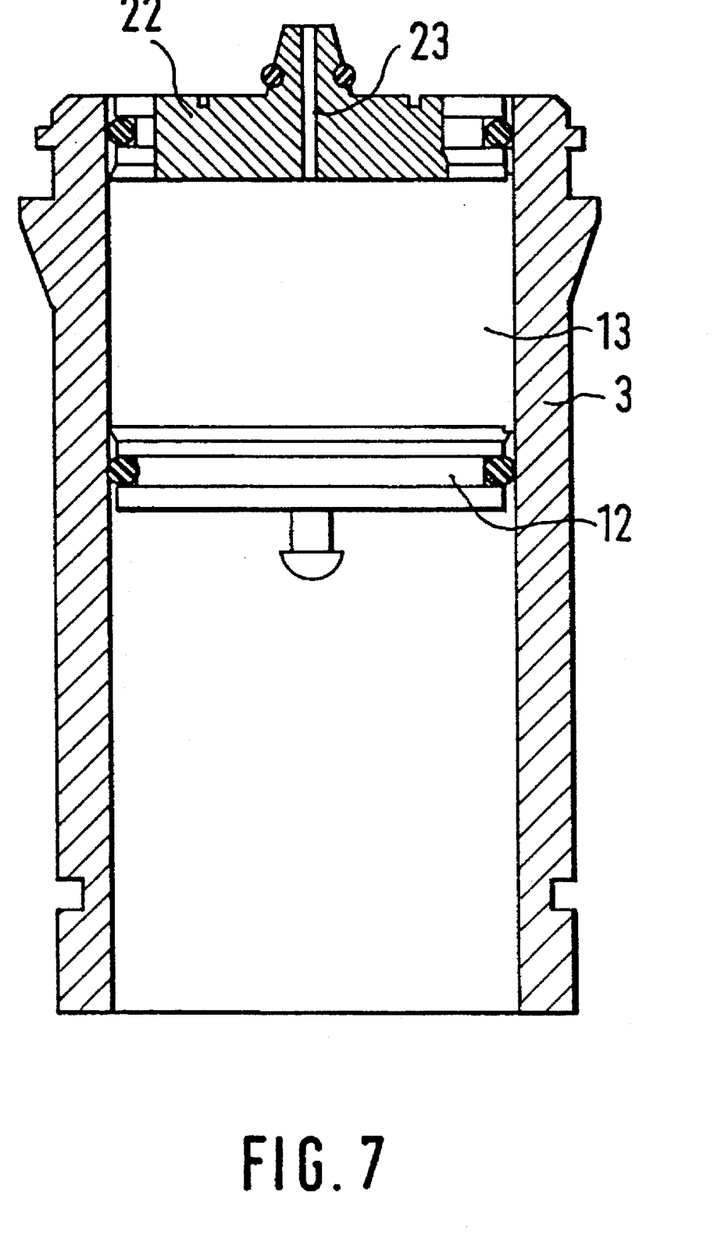

The illustrative example represented in FIGS. 6 and 7 differs from the previously described illustrative embodiment essentially in that a sealing plunger 22 is arranged at the upper end of the lower cylinder part 3, and thus between the discharging plunger 12 and the separating plunger 10. In the state shown in FIGS. 6 and 7, in which the two cylinder parts 2 and 3 are still separate from each other, the sealing plunger 22 seals off the cylinder chamber 13 of the lower cylinder part 3. The sealing plunger 22 accommodated in an axially movable manner in the lower cylinder part 3 likewise has a bore 23 which forms a through-flow channel.

Figure 3:
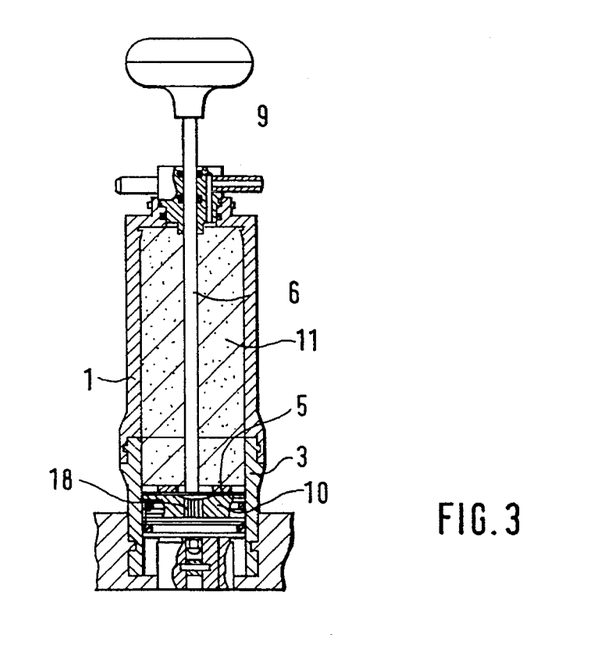

When the cylinder parts 2 and 3 are connected to each other, in accordance with FIG. 2, the separating plunger 10 comes to bear on the sealing plunger 22 and carries the latter along in the direction of the discharging plunger 12 when the mixing plunger 5 is pressed downwards, in accordance with FIG. 3.

The use of the sealing plunger 22 makes it possible to store the liquid, forming a starting material for the bone cement, in a sealed manner in the cylinder chamber 13 of the lower cylinder part 3, without a separate liquid container 14 having to be used for this purpose.

Various illustrative embodiments of the through-flow channels 18 on the separating plunger 10 are represented diagrammatically in FIGS. 8–12.

Figure 8A:
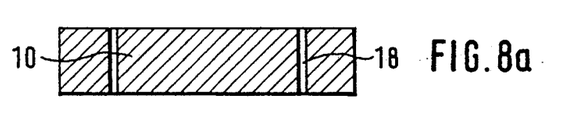
FIGS. 8–12 show different illustrative embodiments of the separating plunger in diagrammatic representation, namely, in each case, in a section a) and in a half plan view b)
Figure 8B:
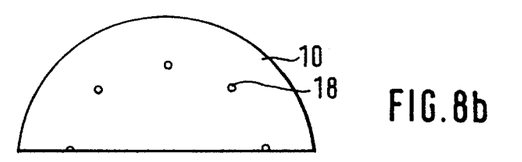

In the example according to FIG. 8, a plurality of bores arranged on a ring form the through-flow channels 18. As a result of this, the liquid monomer penetrates into the pulverulent polymer in a plurality of separate streams, so as to achieve an intensive and thorough mixing.

Figure 9A:
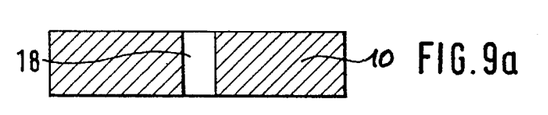
Figure 9B:
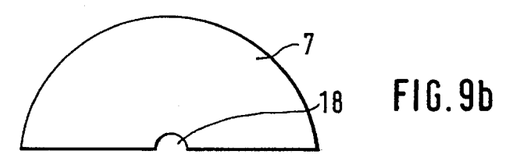

FIG. 9 shows diagrammatically the embodiment also represented in FIG. 6, in which only a central bore is provided as through-flow channel 18 in the separating plunger 10.

Figure 10A:
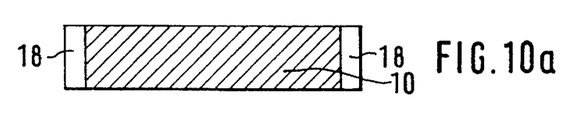
Figure 10B:
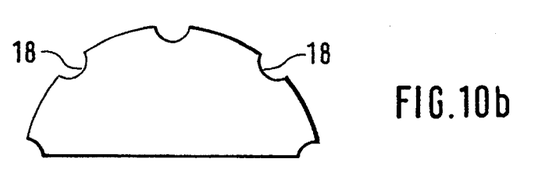

In the example according to FIG. 10, the through-flow channels 18 are formed by recesses at the edge of the separating plunger 10. In this way, a through-flow of the liquid is made possible in the edge area of the mixing cylinder.

Figure 11A:
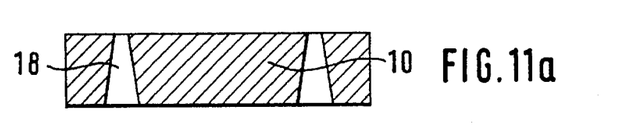
Figure 11B:
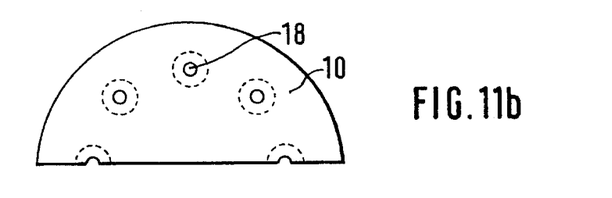

FIG. 11 shows a modification based on FIG. 8. Here too the through-flow channels 18 are formed by a plurality of bores, these tapering towards the discharge-side cylinder chamber 11. An acceleration of the flow of liquid upon passage into the powder is achieved in this way.

Figure 12A:
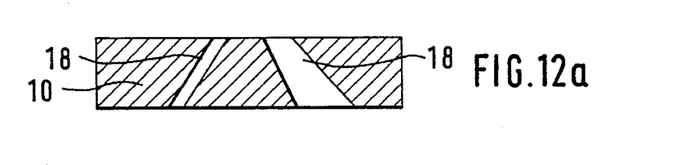
Figure 12B:
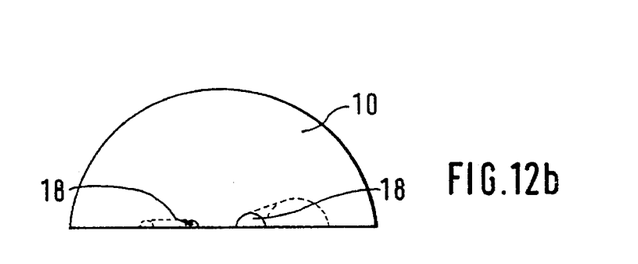

In the embodiment according to FIG. 12, the bores forming the through-flow channels 18 are arranged inclined with respect to the cylinder axis in order to achieve a better mixing. In addition, these bores too can be tapered, as is shown in FIG. 12a.

Figure 13:
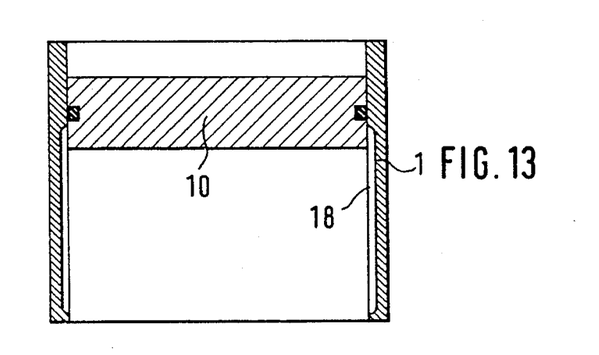
FIG. 13 shows, in a simplified partial longitudinal section, the separating plunger in a cylinder section with grooves in the cylinder wall.

FIG. 13 indicates diagrammatically that the through-flow channels 18 can be formed by longitudinal grooves in the inner wall of the mixing cylinder 1.

We claim:

1. In a device for mixing at least first and second components of a bone cement and for discharging bone cement, the device including a two-part mixing cylinder in which an openworked mixture plunger is moved axially and rotatably by means of an actuation rod emerging in a sealed manner at one cylinder end, the mixing cylinder being closed at the other cylinder end by a releasably locked discharging plunger which is pressed axially into the mixing cylinder in order to discharge the mixed bone cement through an opposite discharge opening, the improvement comprising:

a separating plunger (10) arranged for axial displacement in the mixing cylinder (1) between the mixing plunger (5) and the discharging plunger (12); the separating plunger (10), mixing plunger (5) and discharging plunger (12) being initially disconnected from one another;

the separating plunger being a rigid, imperforable element;

the first component of the bone cement being a pulverulent polymer (30) and the second component of the bone cement being a liquid monomer (15);

a first cylinder chamber (11) extending from a first end of the mixing cylinder (1) and initially containing the first component 30;

a second cylinder chamber (13) disposed between the separating plunger (10) and discharging plunger (12);

a container (14) for the second component (15) of the bone cement being disposed in the second cylinder chamber (13);

the cylinder chambers (11, 13) of the mixing cylinder (1), which are initially separated from each other by the separating plunger (10), being connected to each other via at least one through-flow channel (18) in at least one of said separating plunger and mixing cylinder, whereby upon displacing the mixing plunger toward the second cylinder chamber (13), the separating plunger (10) moves to rupture the container (14) and the second component (15) flows through the at least one channel (18) to mix with the first component (30).

2. The improvement according to claim 1, wherein the at least one through-flow channel (18) is formed by at least one bore in the separating plunger (10).

3. The improvement according to claim 2, wherein there are a plurality of through flow channels (18) in the separating plunger (10), the through-flow channels being configured as a plurality of bores (18).

4. The improvement according to claim 3, wherein at least one of the bores (18) tapers towards the first end of said mixing cylinder (11).

5. The improvement according to claim 3, wherein the bores (18) extend in a direction inclined with respect to the cylinder axis.

6. The improvement of according to claim 2, wherein the at least one bore (18) tapers towards the first end of said mixing cylinder (11).

7. The improvement according to claim 2, wherein the at least one bore (18) extends in a direction inclined with respect to the cylinder axis.

8. The improvement according to claim 1, wherein there are a plurality of through-flow channels which are configured as recesses at the edge of the separating plunger (10).

9. The improvement according to claim 1, wherein there are a plurality of the through-flow channels (18), the through-flow channels being formed by longitudinal grooves in the inner wall of the mixing cylinder (1).

10. The improvement according to claim 1, wherein the actuation rod (6) is connected releasably to the mixing plunger (5), and wherein a guide bush (7) is arranged detachably on the mixing cylinder (1), through which guide bush (7) the actuation rod (6) is guided sealingly and can be replaced by a discharge nozzle (21).

11. The improvement according to claim 10, wherein the releasable connection between the actuation rod (6) and the mixing plunger (5) is formed by a predetermined break point (20).

12. The improvement according to claim 1, wherein an axially movable sealing plunger (22) is arranged between the discharging plunger (12) and the separating plunger (10).

13. The improvement according to claim 1 wherein the first and second cylinder chambers (11, 13) are coupled at a joint (4) with the separating plunger (10) being contained initially within the first cylinder chamber (11) and the discharge plunger being contained initially in the second cylinder chamber (13).

14. The improvement of claim 13, wherein the second component (15) is a liquid.

15. The improvement of claim 14, wherein the joint (4) is a threaded connection.

* * * * *